(12) United States Patent
West et al.

(10) Patent No.: US 9,670,458 B2
(45) Date of Patent: Jun. 6, 2017

(54) METHODS FOR SPERMATOGONIAL STEM CELL (SSC) TRANSFER

(71) Applicant: MICE WITH HORNS, LLC, Delray Beach, FL (US)

(72) Inventors: James West, Nashville, TN (US); Susan M. Majka, Brentwood, TN (US)

(73) Assignee: AGGENETICS, INC., Nashville, TN (US)

( * ) Notice: Subject to any disclaimer, the term of this patent is extended or adjusted under 35 U.S.C. 154(b) by 392 days.

(21) Appl. No.: 14/329,443

(22) Filed: Jul. 11, 2014

(65) Prior Publication Data

US 2015/0018604 A1 Jan. 15, 2015

Related U.S. Application Data

(60) Provisional application No. 61/845,963, filed on Jul. 13, 2013.

(51) Int. Cl.
| | | |
|---|---|---|
| *A61B 17/43* | (2006.01) | |
| *C12N 5/00* | (2006.01) | |
| *C12N 5/071* | (2010.01) | |
| *C12N 5/076* | (2010.01) | |

(52) U.S. Cl.
CPC ........... *C12N 5/0612* (2013.01); *C12N 5/061* (2013.01)

(58) Field of Classification Search
CPC ........ A61D 19/00; A61D 19/02; A61K 35/52; A61K 9/0034; C12N 5/061; C12N 5/06124
USPC .................................. 600/33–35; 800/14–15
See application file for complete search history.

(56) References Cited

U.S. PATENT DOCUMENTS

| | | | |
|---|---|---|---|
| 8,998,793 B2 * | 4/2015 | Oatley ................... | C12N 5/061 435/325 |
| 2005/0034177 A1 | 2/2005 | Readhead et al. | |
| 2007/0011756 A1 | 1/2007 | Shinohara et al. | |
| 2007/0061910 A1 | 3/2007 | Han et al. | |
| 2008/0060091 A1 | 3/2008 | Shinohara et al. | |
| 2011/0302666 A1 | 12/2011 | Hamra | |

OTHER PUBLICATIONS

Matzuk, Martin M. et al., "The biology of infertility: research advances and clinical challenges," *Nature Medicine*, 2008, 14(11):1197-1213.

\* cited by examiner

*Primary Examiner* — John Lacyk
(74) *Attorney, Agent, or Firm* — Saliwanchik, Lloyd & Eisenschenk

(57) ABSTRACT

The present invention provides highly advantageous and efficient methods for spermatogonial stem cell (SSC) transfer for the generation of animals having valuable traits or genetic background.

25 Claims, No Drawings

METHODS FOR SPERMATOGONIAL STEM CELL (SSC) TRANSFER

CROSS-REFERENCE TO A RELATED APPLICATION

This application claims the benefit of U.S. Provisional Application Ser. No. 61/845,963, filed Jul. 13, 2013, which is incorporated herein by reference in its entirety.

BACKGROUND OF THE INVENTION

Spermatogonial stem cell (SSC) transfer is a valuable methodology for generations of genetically modified animals, and has been proposed as a method for preserving genetic traits of commercially valuable animals. Fertility declines in stud bulls after about five years of age, and ongoing researches have been conducted to develop technology for transferring SSC from one bull to another.

In SSC transfer, testis cells from a donor bull testis are obtained either by castration or biopsy. The donor testis cells can be enriched for type Ad spermatogonium through a variety of methods including flow sorting for cell surface markers and growth in culture media. The enriched donor cells are then cultured under conditions allowing expansion of SSCs. Expanded SSCs are injected into the rete testis of a recipient for transplantation. Depending on the animal breed, functional donor spermatozoa cells can be produced in the recipient three to five months after the transplantation.

Currently, a key barrier for SSC transfer is that sperm produced from the recipient can include a mixture of sperm derived from the donor as well as native sperm produced by the recipient. After SSC transfer, the recipient animal continues to produce its own spermatozoa; as a result, even with the best existing SSC transfer practices, after transplantation, less than 50% of the spermatozoa produced by the recipient animal are derived from the donor animal, and more typical percentages of spermatozoa derived from the donor animal are in the range of 1% to 20%.

Attempts have been made to increase the yield of spermatozoa derived from the donor animal after SSC transfer. Existing methods include the use of radiation or chemicals (such as busulfan) to kill native (recipient) stem cells; however, these methods only achieved suboptimal effects. Accordingly, improved methods for SSC transfer are needed.

BRIEF SUMMARY

The present invention provides highly advantageous and efficient methods for spermatogonial stem cell (SSC) transfer for the generation of animals having valuable traits or genetic background. Advantageously, the SSC transfer method of the present invention can effectively produce sperms containing almost 100% of donor-derived sperms (with little or no native sperms of the recipient animal).

In one embodiment, the present invention provides a method for effecting spermatogonial stem cell (SSC) transfer, wherein the method comprises:

providing spermatogonial stem cells (SSCs) from a male donor animal;

introducing the donor SSCs into a reproductive organ of a sterile, hybrid male recipient animal, whereby the sterile, hybrid male recipient produces donor-derived, fertilization-competent, haploid male gametes; and optionally, collecting the donor-derived, fertilization-competent, haploid male gametes produced by the sterile, hybrid male recipient.

In another embodiment, the present invention provides a method for effecting spermatogonial stem cell (SSC) transfer, wherein the method comprises:

providing spermatogonial stem cells (SSCs) from a male donor animal;

introducing the donor SSCs into a reproductive organ of a genetically-modified, sterile male recipient animal, whereby the sterile male recipient produces donor-derived, fertilization-competent, haploid male gametes, and wherein the sterile male recipient animal is genetically modified such that it has an intact spermatogenic compartment but cannot perform spermatogenesis; and optionally, collecting the donor-derived, fertilization-competent, haploid male gametes produced by the sterile male recipient.

In another embodiment, the present invention provides a method for effecting spermatogonial stem cell (SSC) transfer, wherein the method comprises:

providing spermatogonial stem cells (SSCs) from a male donor animal;

introducing the donor SSCs into a reproductive organ of a genetically-modified male recipient animal whereby the recipient produces donor-derived, fertilization-competent, haploid male gametes, wherein the recipient animal is genetically modified such that the native male gametes produced by the recipient animal express at least one detectable biomarker label; optionally, distinguishing the native male gametes produced by the recipient animal from the donor-derived male gametes produced by the recipient animal based on the detectable biomarker label; and optionally, collecting donor-derived, fertilization-competent, haploid male gametes produced by the recipient animal.

In one specific embodiment, the native male gametes produced by the recipient animal express at least one detectable cell surface biomarker (such as cell-surface antigen tag(s)).

In one embodiment, native male gametes produced by the recipient animal express luminescent proteins. In one embodiment, native male gametes produced by the recipient animal are distinguished from the donor-derived male gametes produced by the recipient animal by flow sorting, such as fluorescence activated cell sorting (FACS) and magnetic-activated cell sorting (MACS).

In one embodiment, the donor spermatogonial stem cells (SSCs) embody a genetic background of interest. In one specific embodiment, the donor animal is from the Genus of Bos, including but not limited to, *Bos Taurus* (domestic cattle).

In certain embodiments, the recipient animal can be adult animals or immature animals. In one embodiment, the recipient animal is in puberty.

DETAILED DISCLOSURE

The present invention provides highly advantageous and efficient methods for spermatogonial stem cell (SSC) transfer for the generation of animals having valuable traits or genetic background.

In one embodiment, the present invention provides a method for effecting spermatogonial stem cell (SSC) transfer, wherein the method comprises:

providing spermatogonial stem cells (SSCs) from a male donor animal;

introducing the donor SSCs into a reproductive organ of a sterile male recipient animal, whereby the sterile male recipient produces donor-derived, fertilization-competent, haploid male gametes; and optionally, collecting the donor-derived, fertilization-competent, haploid male gametes produced by the sterile male recipient.

In certain embodiments, the SSC transfer method uses sterile, hybrid male recipient animals or sterile male recipient animals that have been genetically modified to have heritable male sterility.

In one embodiment, the recipient male animal is genetically modified such that it has an intact spermatogenic compartment but cannot perform spermatogenesis.

In certain embodiments, the sterile recipient animal can be produced via deletion or inactivating mutations of genes including, but not limited to, Deleted-in-Azoospermia like (DAZL); protamine genes (e.g., PRM1, PRM2) associated with DNA packaging in the sperm nucleus; genes in the azoospermia factor (AZF) region of the Y chromosome (such genes include, but are not limited to, USP9Y); and genes associated with male meiosis (such genes include, but are not limited to, HORMA domain-containing protein 1 (HORMAD1)). In another embodiment, the sterile recipient animal can be produced via genetic mutation(s) associated with sertoli cell-only syndrome (such genetic mutation includes mutations in USP9Y).

In one specific embodiment, the recipient male animal is genetically modified such that it does not express functional Deleted-in-Azoospermia like (DAZL) protein. In one specific embodiment, the recipient male animal is genetically modified such that the DAZL gene is deleted.

In one specific embodiment, the recipient male animal is genetically modified such that the DAZL gene does not encode functional DAZL protein.

As used herein, an inactivating mutation refers to any mutation (genetic alteration of a DNA molecule) that leads to an at least 30% reduction of function of the protein encoded by the DNA molecule. In one embodiment, a 100%-inactivating mutation is any mutation (genetic alteration of a DNA molecule) that leads to a complete loss of function of the protein encoded by the DNA molecule. In one embodiment, the present invention provides a method for effecting spermatogonial stem cell (SSC) transfer, wherein the method comprises:

providing spermatogonial stem cells (SSCs) from a male donor animal;

introducing the donor SSCs into a reproductive organ of a sterile, hybrid male recipient animal, whereby the sterile, hybrid male recipient produces donor-derived, fertilization-competent, haploid male gametes; and optionally, collecting the donor-derived, fertilization-competent, haploid male gametes produced by the sterile, hybrid male recipient.

The term "hybrid animal," as used herein, refers to a crossbred animal with parentage of two different species. Hybrid male animals are usually sterile and cannot produce fertilization-competent, haploid male gametes. Examples of hybrid animals include, but are limited to, mules (a cross between a horse and a donkey), ligers (a cross between a lion and a tiger), yattles (a cross between a yak and a buffalo), dzo (a cross between a yak and a bull), and hybrid animals that are crosses between servals and ocelots/domestic cats. Hybrid animals include animals with 50:50 mixtures of parentage, as well as animals with mixtures different from 50:50 parentage, provided that the hybrid offspring of such mixtures is sterile.

In another embodiment, the present invention provides a method for effecting spermatogonial stem cell (SSC) transfer, wherein the method comprises:

providing spermatogonial stem cells (SSCs) from a male donor animal;

introducing the donor SSCs into a reproductive organ of a genetically-modified, sterile male recipient animal, whereby the sterile male recipient produces donor-derived, fertilization-competent, haploid male gametes, and wherein the sterile male recipient animal is genetically modified such that it has an intact spermatogenic compartment but cannot perform spermatogenesis; and optionally, collecting the donor-derived, fertilization-competent, haploid male gametes produced by the sterile male recipient.

In another embodiment, the present invention provides a method for effecting spermatogonial stem cell (SSC) transfer, wherein the method comprises:

providing spermatogonial stem cells (SSCs) from a male donor animal;

introducing the donor SSCs into a reproductive organ of a genetically-modified male recipient animal whereby the recipient produces donor-derived, fertilization-competent, haploid male gametes, wherein the recipient animal is genetically modified such that the native male gametes produced by the recipient animal express at least one detectable biomarker label; optionally, distinguishing the native male gametes produced by the recipient animal from the donor-derived male gametes produced by the recipient animal based on the detectable biomarker label; and optionally, collecting donor-derived, fertilization-competent, haploid male gametes produced by the recipient animal.

In one specific embodiment, the native male gametes produced by the recipient animal express at least one detectable cell surface biomarker (such as cell-surface antigen tag(s)).

In one embodiment, native male gametes produced by the recipient animal express luminescent proteins. In one embodiment, native male gametes produced by the recipient animal are distinguished from the donor-derived male gametes produced by the recipient animal by flow sorting, such as fluorescence activated cell sorting (FACS) and magnetic-activated cell sorting (MACS).

In one embodiment, the genetically-modified recipient male animal comprises a reporter gene for expression on the cell surface of native male gametes. In certain embodiments, the reporter gene encodes a luminescent protein.

The term "luminescent protein," as used herein, refers to a protein that emits light. Luminescent proteins useful according to the present invention include, but are not limited to, fluorescent proteins including, but not limited to, green fluorescent protein, yellow fluorescent protein, cyan fluorescent protein, and red fluorescent protein; and phosphorescent proteins. Fluorescent proteins are members of a class of proteins that share the unique property of being self-sufficient to form a visible wavelength chromophore from a sequence of three amino acids within their own polypeptide sequence. A variety of luminescent proteins, including fluorescent proteins, are publicly known. Fluorescent proteins useful according to the present invention include, but are not limited to, the fluorescent proteins disclosed in U.S. Pat. No. 7,160,698, U.S. Application Publication Nos. 2009/0221799, 2009/0092960, 2007/0204355, 2007/0122851, 2006/0183133, 2005/0048609, 2012/0238726, 2012/0034643, 2011/0269945, 2011/0223636, 2011/0152502, 2011/0126305, 2011/0099646, 2010/0286370, 2010/0233726, 2010/0184116, 2010/

0087006, 2010/0035287, 2007/0021598, 2005/0244921, 2005/0221338, 2004/0146972, and 2001/0003650, all of which are hereby incorporated by reference in their entireties.

In one embodiment, donor SSCs are introduced into the testis of the male recipient animal.

In one embodiment, male gametes produced by the recipient animal are sperm.

In one embodiment, the donor spermatogonial stem cells (SSCs) embody a genetic background of interest. In one specific embodiment, the donor animal is from the Genus of *Bos*, including but not limited to, *Bos Taurus* (domestic cattle).

In certain embodiments, the recipient animal can be adult animals or immature animals. In one embodiment, the recipient animal is in puberty.

In a further embodiment, the present invention further comprises the step of fertilizing an egg from an animal species of interest with the donor-derived, fertilization-competent, haploid male gamete produced by the recipient animal. Methods of fertilization of eggs are known in the art, and include, but are not limited to, intracytoplasmic sperm injection (ICSI) and round spermatid injection (ROSI).

Donor and Recipient Animals

Parentages of the recipient hybrid animal, the recipient animal, and/or the donor animal can be of any animal species including, but not limited to, species of cats; mice; rats; wolves; coyotes; dogs; chinchillas; deer; muskrats; lions; tigers; pigs; hamsters; horses; cattle; sheep; goats; ducks; geese; chickens; primates such as apes, chimpanzees, orangutans, monkeys; and humans.

Parentages of the recipient hybrid animal can be of 50:50 percentage, or of any mixture of parentages (including but not limited to 60:40; 70:30; 80:20:90:10; and any mixture in between), provided that the mixture of parentages maintains the sterility of the hybrid animal.

In certain embodiments, one or both parentages of the recipient hybrid animal, the recipient animal, and/or the donor animal can be of any vertebrates, including fish, amphibians, birds, and mammals. In certain embodiments, one or both parentages of the recipient hybrid animal, the recipient animal, and/or the donor animal are not a human.

In certain embodiments, one or both parentages of the recipient hybrid animal, the recipient animal, and/or the donor animal can be from any family of Equidae, Bovidae, Canidae, Felidae, and Suidae.

In certain embodiments, one or both parentages of the recipient hybrid animal, the recipient animal, and/or the donor animal can be from the genus of *Equus* including, but not limited to, Subgenus *Equus*, Subgenus *Asinus*, Subgenus *Dolichohippus*, and Subgenus *Hippotigris*.

In certain embodiments, one or both parentages of the recipient hybrid animal, the recipient animal, and/or the donor animal can be from the genus of *Equus* including, but not limited to, *Equus ferus* (wild horse), including but not limited to, *Equus ferus caballus* (domestic horse) and *Equus ferus przewalskii* (Przewalski's horse or Mongolian Wild Horse or takhi); *Equus africanus* (African Wild Ass), including but not limited to, *Equus africanus africanus* (Nubian Wild Ass), *Equus africanus asinus* (Domestic Donkey), and *Equus africanus somalicus* (Somali Wild Ass); *Equus hemionus* (Onager or Asiatic Ass), including but not limited to, *Equus hemionus hemionus* (Mongolian Wild Ass, Dziggetai or Gobi Kulan), *Equus hemionus khur* (Indian Wild Ass or Khur), *Equus hemionus kulan* (Turkmenian Kulan), and *Equus hemionus onager* (Persian Onager); *Equus kiang* (Kiang), including but not limtied to, *Equus kiang chu* (Northern Kiang), *Equus kiang kiang* (Western Kiang), *Equus kiang holdereri* (Eastern Kiang), and *Equus kiang polyodon* (Southern Kiang); *Equus grevyi* (Grevy's Zebra), including but not limited to, *Equus quagga* (Plains Zebra), *Equus quagga boehmi* (Grant's Zebra), *Equus quagga borensis* (Maneless Zebra), *Equus quagga chapmani* (Chapman's Zebra), *Equus quagga crawshayi* (Crawshay's Zebra), *Equus quagga burchellii* (Burchell's Zebra), and *Equus quagga selousi* (Selous' Zebra); *Equus* zebra L.1(758 Mountain Zebra), including but not limited to, *Equus zebra hartmannae* (Hartmann's Mountain Zebra), and *Equus zebra* zebra (Cape Mountain Zebra); and *Equus major* Boule (nomen dubium).

In certain embodiments, one or both parentages of the recipient hybrid animal, the recipient animal, and/or the donor animal can be from the genus of *Bovidae* including, but not limited to, Subfamily Bovinae; Subfamily Cephalophinae; Subfamily Hippotraginae; Subfamily Antilopinae; Subfamily Caprinae; Subfamily Reduncinae; Subfamily Aepycerotinae; Subfamily Peleinae; Subfamily Alcelaphinae; and Subfamily Pantholopinae.

In certain embodiments, one or both parentages of the recipient hybrid animal, the recipient animal, and/or the donor animal can be from *Bovidae*, including but not limited to, Tribe Boselaphini, including but not limited to, Genus *Tetracerus*, including but not limited to, *Tetracerus quadricornis* (four-horned antelope); Genus *Boselaphus*, including but not limited to, *Boselaphus tragocamelus* (blue bull); Tribe Bovini, including but not limited to, Genus *Bubalus*, including but not limited to, *Bubalus bubalis* (water buffalo), *Bubalus arnee* (Wild Asian water buffalo), *Bubalus depressicornis* (Lowland anoa), *Bubalus quarlesi* (Mountain anoa), and *Bubalus mindorensis* (Tamaraw); Genus *Bos*, including but not limited to, *Bos javanicus* (Banteng), *Bos gaurus* (Gaur), *Bos frontalis* (Gayal, domestic gaur), *Bos mutus* (yak), *Bos grunniens* (yak), *Bos taurus* (domestic cattle), and *Bos indicus* (Domestic zebu); Genus *Pseudoryx*, including but not limited to, *Pseudoryx nghetinhensis* (Saola); Genus *Syncerus*, including but not limtied to, *Syncerus caffer* (African buffalo); and Genus *Bison*, including but not limited to, *Bison bison* (American bison) and *Bison bonasus* (Wisent); Tribe Strepsicerotini, including but not limited to, Genus *Tragelaphus* (antelope-like), including but not limited to, *Tragelaphus eurycerus* (Bongo), *Tragelaphus strepsiceros* (Greater kudu), *Tragelaphus scriptus* (Kéwel), *Tragelaphus sylvaticus* (Imbabala), *Tragelaphus imberbis* (Lesser kudu), *Tragelaphus buxtoni* (Mountain nyala), *Tragelaphus angasii* (Nyala), and *Tragelaphus spekeii* (Sitatunga); and Genus *Taurotragus*, including but not limited to, *Taurotragus onyx* (Common eland) and *Taurotragus derbianus* (Giant eland).

In certain embodiments, one or both parentages of the recipient hybrid animal, the recipient animal, and/or the donor animal can be from Canidae, including but not limited to, Caninae.

In certain embodiments, one or both parentages of the recipient hybrid animal, the recipient animal, and/or the donor animal can be from Canidae, including but not limited to, Tribe Canini, including but not limited to, Genus *Canis*, including but not limited to, *Canis Lupus* (grey wolf), *Canis lupus familiaris* (domestic dog), *Canis lupus dingo* (Dingo), *Canis latrans* (Coyote, also called prairie wolf), *Canis simensis* (Ethiopian wolf, also called Abyssinian wolf, simien fox and simien jackal), *Canis aureus* (Golden jackal), *Canis adustus* (Side-striped jackal), and *Canis mesomelas* (Black-backed jackal); Genus *Cuon*, including but not limited to, *Cuon alpinus* and *Canis alpinus* (also called Asian wild dog); Genus *Lycaon*, including but not limited to, *Lycaon pictus* (African wild dog, also called African hunting dog); Genus *Atelocynus*, including but not limited to, *Atelocynus microtis* (short-eared dog); Genus *Cerdocyon*, including but not limited to, *Cerdocyon thous* (Crab-eating fox); Genus *Lycalopex* (*Pseudalopex*), including but not limited to, *Lycalopex culpaeus* (Culpeo), *Lycalopex fulvipes* (Darwin's fox), *Lycalopex griseus* (South American gray fox), *Lycalopex gymnocercus* (Pampas fox), *Lycalopex sechurae* (Sechura fox), and *Lycalopex vetulus* (Hoary fox); Genus *Chrysocyon*, including but not limited to, *Chrysocyon brachyurus* (Maned wolf); and Genus *Speothos*, including but not limited to, *Speothos venaticus* (bush dog); Tribe Vulpini, including but not limited to, Genus *Vulpes*, including but not limited to, *Vulpes lagopus* (Arctic fox), *Vulpes vulpes* (red fox), *Vulpes velox* (swift fox), *Vulpes macrotis* (kit fox), and *Vulpes corsac* (Corsac fox); and Genus *Urocyon*, including but not limited to, *Urocyon cinereoargenteus* (gray fox), *Urocyon littoralis* (island fox), and *Urocyon* sp. (Cozumel fox); and Basal Caninae, including but not limited to, Genus *Otocyon*, including but not limited to, *Otocyon megalotis* (bat-eared fox); and Genus *Nyctereutes*, including but not limited to, *Nyctereutes procyonoides* (raccoon dog).

In certain embodiments, one or both parentages of the recipient hybrid animal, the recipient animal, and/or the donor animal can be from Family Felidae; including but not limited to, Subfamily Pantherinae, including but not limited to, Genus *Panthera*, including but not limited to, lion (*Panthera leo*), jaguar (*Panthera onca*), leopard (*Panthera pardus*), and tiger (*Panthera tigris*); Genus *Uncia*, including but not limited to, snow leopard (*Uncia uncia*); Genus *Neofelis*, including but not limited to, clouded leopard (*Neofelis nebulosa*) and sunda clouded leopard (*Neofelis diardi*); Subfamily Felinae, including but not limited to, Genus *Pardofelis*, including but not limited to, marbled cat (*Pardofelis marmorata*); Genus *Catopuma*, including but not limited to, bay cat (*Catopuma badia*) and Asian golden cat (*Catopuma temminckii*); Genus *Leptailurus*, including but not limited to, *Serval* (*Leptailurus serval*); Genus *Caracal*, including but not limited to, *Caracal* (*Caracal caracal*); Genus *Profelis*, including but not limited to, African golden cat (*Profelis aurata*); Genus *Leopardus*, including but not limited to, Pantanal cat (*Leopardus braccatus*), Colocolo (*Leopardus colocolo*), Geoffroy's cat (*Leopardus geoffroyi*), Kodkod (*Leopardus guigna*), Andean mountain cat (*Leopardus jacobitus*), Pampas cat (*Leopardus pajeros*), Ocelot (*Leopardus pardalis*), Oncilla (*Leopardus tigrinus*), and Margay (*Leopardus wiedii*); Genus *Lynx*, including but not limited to, Canadian lynx (*Lynx canadensis*), Eurasian lynx (*Lynx lynx*), Iberian lynx (*Lynx pardinus*), and Bobcat (*Lynx rufus*); Genus *Puma*, including but not limited to, Cougar (*Puma concolor*) and Jaguarundi (*Puma yagouaroundi*); Genus *Acinonyx*, including but not limited to, Cheetah (*Acinonyx jubatus*); Genus *Prionailurus*, including but not limited to, leopard cat (*Prionailurus bengalensis*); Iriomote cat (*Prionailurus bengalensis iriomotensis*), flat-headed cat (*Prionailurus planiceps*), rusty-spotted cat (*Prionailurus rubiginosus*), and fishing cat (*Prionailurus viverrinus*); Genus *Otocolobus*, including but not limited to, Pallas's cat (*Otocolobus manul*); and Genus *Felis*, including but not limited to, Chinese mountain cat (*Felis bieti*), domestic cat (*Felis catus*), jungle cat (*Felis chaus*), sand cat (*Felis margarita*), black-footed cat (*Felis nigripes*), and wildcat (*Felis silvestris*).

In certain embodiments, one or both parentages of the recipient hybrid animal, the recipient animal, and/or the donor animal can be from Family Suidae, including but not limited to, Subfamily Suinae, including but not limited to, Tribe Babyrousini, including but not limited to, Genus *Babyrousa*, including but not limited to, *Babyrousa babyrussa* (Golden Babirusa), *Babyrousa celebensis* (Sulawesi Babirusa), and *Babyrousa togeanensis* (Togian Babirusa); Tribe Potamochoerini, including but not limited to, Genus *Hylochoerus*, including but not limited to, *Hylochoerus meinertzhageni* (Giant Forest Hog); and Genus *Potamochoerus*, including but not limited to, *Potamochoerus larvatus* (Bushpig) and *Potamochoerus porcus* (Red River Hog); Tribe Suini, including but not limited to, Genus *Sus*, including but not limited to, *Sus ahoenobarbus* (Palawan Bearded Pig), *Sus barbatus* (Bornean bearded pig), *Sus bucculentus* (Vietnamese Warty Pig), *Sus cebifrons* (Visayan Warty Pig), *Sus celebensis* (Celebes Warty Pig), *Sus heureni* (Flores Warty Pig), *Sus oliveri* (Mindoro Warty Pig), *Sus philippensis* (Philippine Warty Pig), *Sus scrofa* (also called *S. domesticus*, Domestic pig), and *Sus verrucosus* (Javan Warty Pig); Tribe Phacochoerini, including but not limited to, Genus *Phacochoerus*, including but not limited to, *Phacochoerus aethiopicus* (Cape, Somali or Desert Warthog) and *Phacochoerus africanus* (Common Warthog); Tribe *incertae sedis*, including but not limited to, Genus *Porcula*, including but not limited to, *Porcula salvania* (Pygmy Hog).

Transplantation of Spermatogonial Stem Cells

Mammalian spermatogonial stem cells (SSCs) self-renew and produce daughter cells that commit to differentiate into spermatozoa throughout adult life of the male. SSCs can be identified by functional assays known in the art, such as transplantation techniques in which donor testis cells are injected into the seminiferous tubules of a sterile recipient.

In one embodiment, donor spermatogonial stem cells can be cryopreserved and/or cultured in vitro. Frozen spermatogonial stem cells can be grown in vitro and cryopreserved again during the preservation period.

SSCs can be cultured in serum-containing or serum-free medium. In one embodiment, the cell culture medium comprises Dulbecco's Modified Eagle Medium (DMEM), and optionally, fetal calf serum.

In certain embodiments, SSC culture medium can comprise one or more ingredients including, but not limited to, glial cell-derived neurotrophic factor (GDNF), fibroblast growth factor-2 (FGF2), leukemia inhibitory factor (LIF), insulin-like growth factor-I (IGF-I), epidermal growth factor (EGF), stem cell factor (SCF), B27-minus vitamin A, Ham's F12 nutrient mixture, 2-mercaptoethanol, and L-glutamine.

Methods for transplanting spermatogonial stem cells into recipient reproductive organs (such as, the testis) are known in the art. Transplantation can be performed by direct injection into seminiferous tubules through microinjection, or by injection into efferent ducts through microinjection, thereby allowing SSCs to reach the rete testis of the recipient. The transplanted spermatogonial stem cells adhere to the tube wall of the recipient seminiferous tubules, and then differentiate and develop into spermatocytes, spermatids and spermatozoa, and finally mature following transfer to the epididymis.

Methods for the introduction of one or more SSCs into a recipient male also include injection into the vas deferens and epididymis or manipulations on fetal or juvenile testes, techniques to sever the seminiferous tubules inside the testicular covering, with minimal trauma, which allow injected cells to enter the cut ends of the tubules. Alternatively, neonatal testis (or testes), which are still undergoing development, can be used.

EXAMPLES

Following are examples that illustrate procedures and embodiments for practicing the invention. The examples should not be construed as limiting.

Example 1—Spermatogonial Stem Cells (SSC) Transfer with the Use of Sterile Hybrids as Recipients Many commercially valuable animal breeds can be bred to closely related species, resulting in hybrid offspring with male sterility. For instance, cow/yak hybrids result in sterile dzo; horse/donkey crosses result in sterile mules; serval or ocelot/domestic cat crosses produce sterile hybrids. Parentages of hybrid animals can be 50:50, as well as mixtures different from 50:50, including, but not limited to 60:40; 70:30; 80:20: or 90:10, respectively, provided the mixture of parentages maintains the sterility of the hybrid offspring In each of these cases, male sterility is caused by failure of spermatogenesis resulting from failure of meiosis as the parental chromosomes are different enough that they do not pair up correctly to allow production of spermatozoa. Nevertheless, all of the cellular machinery (e.g., Sertoli cells, androgen binding protein) needed to make spermatozoa is present and functional in the sterile, half-breed recipient animal. Also, spermatogenesis in the recipient animal can proceed using donor SSCs from closely related breeds.

In one embodiment in accordance with the present invention, with the use of sterile hybrids as recipients of SSCs, all of the sperms produced by the sterile recipient animal are from the donor animal (the sterile recipient is incapable of making functional sperms carrying its own genetic information).

In certain embodiments, the recipient animal and the donor animal are from the same taxonomic family, sub-family, genus, or sub-genus. In one embodiment, Bovid spermatozoa can be produced in the recipient Dzo. In another embodiment, spermatozoa from the genus of Bos can be produced in the recipient Dzo. One criterion for the selection of donor animal and the recipient animal is based on functional compatibility between the donor and recipient spermatogenesis physiology (e.g., number of division cycles, expected growth factors).

An example of SSC transfer using sterile hybrids as recipient animals is illustrated as follows. Briefly, a punch biopsy of the testis of a stud bull is obtained, flow-sorted for SSC markers on day 1 to enrich for the desired cell population, then cultured extensively to both expand the SSC population and to ensure that only cells capable of self-renewal remain in culture. Cells can be frozen and preserved at this stage. A recipient Dzo (yak/bull hybrid) in mid puberty is placed under general anesthesia. The rete testis is imaged with ultrasound, a catheter is placed in the rete testis, and donor SSCs from the stud bull are introduced into the recipient Dzo. As the recipient is in mid-puberty, cellular niches for SSC exist but have not been filled with the native (non-functional) SSCs. Four to five months after the SSC transfer, sperms of the recipient Dzo are collected. After the SSC transfer, all of the sperms collected from the Dzo are derived from the donor stud bull.

Example 2—Spermatogonial Stem Cell (SSC) Transfer with the Use of Recipient Animals Genetically Modified to Have Spermatoza Identifiable by Flow-Sorting In one embodiment, the SSC transfer is performed using recipient animals genetically modified such that their spermatozoa express markers that can be easily identified by flow sorting. Spermatozoa identifiable by flow sorting include spermatozoa expressing fluorescent proteins and spermatozoa expressing unique cell-surface markers that can be detected by antibody.

An example of SSC transfer using recipient animals genetically modified to have spermatozoa identifiable by flow-sorting is illustrated as follows. Briefly, a punch biopsy of the testis of a stud bull is obtained, flow-sorted for SSC markers on day 1 to enrich for the desired cell population, then cultured extensively to both expand the SSC population and to ensure that only cells capable of self-renewal remain in culture. Cells can be frozen and preserved at this stage. A recipient bull in mid puberty, genetically modified to express fluorescent proteins in the acrosome cap, is placed under general anesthesia. The rete testis of the recipient bull is imaged with ultrasound, a catheter is placed in the rete testis, and SSCs from the donors are introduced. As the recipient is in mid-puberty, cellular niches for SSC exist but have not been filled with the native SSCs. Four to five months after the SSC transfer, sperms from the recipient are collected and flow sorted; fluorescent sperms, which are native sperms carrying the genetic information of the recipient animal, are discarded. Non-fluorescent sperms include native sperms in which the acrosome reaction has initiated. 100% of the non-fluorescent viable sperms are derived from the donor stud bull. The sperms produced by the recipient animal need not be genetically modified.

Example 3—Spermatogonial Stem Cell (SSC) Transfer with the Use of Recipient Animals Genetically Modified for Male Sterility In one embodiment, in order to allow for improved recovery of donor semen in SSC transfer, recipient animals are genetically modified to have heritable male sterility. Heritable male sterility can be caused by having an intact spermatogenic compartment with failure of spermatogenesis. In mice, over 100 genes can disrupt sperm development or function (Matzuk et al.). Rats with naturally occurring mutations in the Deleted-in-Azoospermia like (DAZL) gene are used for SSC transfer for experimental models. An example of SSC transfer using recipient animals genetically modified to have male sterility is illustrated as follows. Briefly, a genetic modification is introduced to the male recipient animal such that the modified recipient has an intact spermatogenic compartment, but cannot perform spermatogenesis. In one specific embodiment, the male recipient animal comprises a DAZL deletion. DAZL mutant or knockout cattle are created using any genetic modification technology, and maintained in the heterozygote state. Sterile males are created by crossing two heterozygote DAZL knockout parents.

Specifically, a punch biopsy of the testis of a valuable stud bull is obtained, flow-sorted for SSC markers on day 1 to enrich for the desired cell population, then cultured extensively to both expand the SSC population and to ensure that only cells capable of self renewal remain in culture. Cells can be frozen and preserved at this stage. A recipient bull in mid puberty, with homozygous DAZL knockout, is placed under general anesthesia. The rete testis of the recipient is imaged with ultrasound, a catheter is placed in the rete testis, and SSCs are introduced into the rete testis. As the recipient is in mid-puberty, cellular niches for SSC exist, but have not been filled with the native SSC. Four or five months after the SSC transfer, sperms are collected and flow sorted; all of the collected sperms are derived from the donor stud bull. The sperms produced by the recipient animal need not be genetically modified.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

REFERENECE

Matzuk M M, Lamb D J. The biology of infertility: research advances and clinical challenges. *Nat Med.* 2008; 14(11):1197-1213.

We claim:

1. A method for generating fertilization-competent haploid male gametes, wherein the method comprises:
   providing spermatogonial stem cells (SSCs) from a male donor animal;
   providing a sterile, hybrid male recipient animal, wherein the hybrid animal has at least one parentage that is from the same genus as the donor animal; and
   introducing the donor SSCs into a reproductive organ of the sterile, hybrid male recipient animal that produces donor-derived, fertilization-competent, haploid male gametes; and, optionally,
   collecting the donor-derived, fertilization-competent, haploid male gametes produced by the sterile, hybrid male recipient.

2. The method, according to claim 1, wherein the donor animal is selected from Equidae, Bovidae, Canidae, Felidae, and Suidae.

3. The method, according to claim 1, wherein the donor animal is from the Genus of Bos.

4. The method, according to claim 1, wherein the male reproductive organ is testis.

5. The method, according to claim 1, wherein the male gametes produced by the recipient are sperm.

6. The method, according to claim 1, wherein the recipient animal is in puberty.

7. A method for generating fertilization-competent haploid male gametes, wherein the method comprises:
   providing spermatogonial stem cells (SSCs) from a male donor animal;
   providing a recipient animal that is genetically-modified such that the native male gametes produced by the recipient animal express at least one detectable biomarker label; and
   introducing the donor SSCs into a reproductive organ of a genetically-modified male recipient animal that produces donor-derived, fertilization-competent, haploid male gametes,
   collecting donor-derived, fertilization-competent, haploid male gametes that lack the biomarker label; and
   distinguishing the native male gametes produced by the recipient animal from the donor-derived male gametes produced by the recipient animal based on the detectable biomarker label.

8. The method, according to claim 7, wherein the detectable biomarker label is on the cell surface of the native male gametes produced by the recipient animal.

9. The method, according to claim 7, wherein the detectable biomarker label is a florescent protein, a luminescent protein, or an antigen tag.

10. The method, according to claim 9, wherein the native male gametes produced by the recipient animal are distinguished from the donor-derived male gametes produced by the recipient animal by fluorescence activated cell sorting (FACS) or magnetic-activated cell sorting (MACS).

11. The method, according to claim 7, wherein the donor animal is selected from Equidae, Bovidae, Canidae, Felidae, and Suidae.

12. The method, according to claim 7, wherein the donor animal is from the Genus of Bos.

13. The method, according to claim 7, wherein at least one parentage of the hybrid recipient animal is from the same genus as the donor animal.

14. The method, according to claim 7, wherein the male reproductive organ is testis.

15. The method, according to claim 7, wherein the male gametes produced by the recipient are sperm.

16. The method, according to claim 7, wherein the recipient animal is in puberty.

17. A method for generating fertilization-competent haploid male gametes wherein the method comprises:
   providing spermatogonial stem cells (SSCs) from a male donor animal;
   providing a sterile male recipient animal that is genetically-modified such that the animal has an intact spermatogenic compartment but cannot perform spermatogenesis, wherein the recipient animal contains a deletion or an inactivating mutation in a gene selected from Deleted-in-Azoospermia like (DAZL); protamine genes associated with DNA packaging in the sperm nucleus; genes in the azoospermia factor (AZF) region of the Y chromosome; and genes associated with male meiosis;

introducing the donor SSCs into a reproductive organ of the genetically-modified, sterile male recipient animal that produces donor-derived, fertilization-competent, haploid male gametes; and, optionally, collecting the donor-derived, fertilization-competent, haploid male gametes produced by the sterile male recipient.

18. The method, according to claim 17, wherein the recipient animal contains a deletion or an inactivating mutation in a gene selected from Deleted-in-Azoospermia like (DAZL), PRM1, PRM2, USP9Y, and HORMAD1.

19. The method, according to claim 17, wherein the donor animal is selected from Equidae, Bovidae, Canidae, Felidae, and Suidae.

20. The method, according to claim 17, wherein the donor animal is from the Genus of Bos.

21. The method, according to claim 17, wherein at least one parentage of the hybrid recipient animal is from the same genus as the donor animal.

22. The method, according to claim 17, wherein the male reproductive organ is testis.

23. The method, according to claim 17, wherein the male gametes produced by the recipient are sperm.

24. The method, according to claim 17, wherein the recipient animal is in puberty.

25. The method according to claim 1, further comprising donor SSC that embody a genetic background of interest.

\* \* \* \* \*

UNITED STATES PATENT AND TRADEMARK OFFICE
CERTIFICATE OF CORRECTION

PATENT NO.        : 9,670,458 B2
APPLICATION NO.   : 14/329443
DATED             : June 6, 2017
INVENTOR(S)       : James West and Susan M. Majka It is certified that error appears in the above-identified patent and that said Letters Patent is hereby corrected as shown below:

In the Specification

Column 6,
Line 50, "Taurotragus onyx" should read -- Taurotragus oryx --.

Column 9,
Line 6, "Stem Cells (SSC)" should read -- Stem Cell (SSC) --.

Signed and Sealed this
Tenth Day of July, 2018

Andrei Iancu
*Director of the United States Patent and Trademark Office*